United States Patent [19]

Morrison

[11] 3,978,853
[45] Sept. 7, 1976

[54] ANKLE HITCH

[75] Inventor: Robert D. Morrison, Worthington, Ohio

[73] Assignee: Morrison Medical Products Company, Columbus, Ohio

[22] Filed: June 4, 1975

[21] Appl. No.: 583,588

[52] U.S. Cl. ............................................. 128/84 R
[51] Int. Cl.² ........................................... A61F 5/04
[58] Field of Search ................. 128/84, 85, 166, 75

[56] References Cited
UNITED STATES PATENTS

| | | | |
|---|---|---|---|
| 491,271 | 2/1893 | Rowley | 128/85 |
| 2,191,097 | 2/1940 | Morrison | 128/85 |
| 2,198,908 | 4/1940 | Ellis | 128/84 R |
| 2,198,995 | 4/1940 | Gray | 128/84 R |
| 3,477,428 | 11/1969 | Hare | 128/85 |
| 3,618,598 | 11/1971 | Davis | 128/85 |
| 3,680,551 | 8/1972 | Bell et al. | 128/84 R |
| 3,720,206 | 3/1973 | Walker et al. | 128/84 R |

Primary Examiner—John D. Yasko
Attorney, Agent, or Firm—Frank H. Foster

[57] ABSTRACT

An ankle hitch for securing a human foot in attachment to a traction mechanism. The ankle hitch has a first relatively longer, flexible strap having a ring fastener secured at each of its opposite ends. A pair of relatively shorter heel straps are each secured at one end to the central portion of the first strap, extend at opposite 70° angles from the first strap and each has a ring fastener secured at its opposite end. A foam layer is detachably fastened to the straps for interposition between the straps and the foot. The straps have an effective length which permits the first strap to be wrapped forwardly around the ankle of the foot, crossed upon the instep of the foot and extend downwardly beyond the bottom of the foot and the heel straps to extend downwardly and forwardly so that all four of the ring fasteners are brought together beneath the foot and in substantial alignment with the longitudinal axis of the leg.

10 Claims, 7 Drawing Figures

ANKLE HITCH

BACKGROUND OF THE INVENTION

This application relates generally to medical equipment and more particularly to an ankle hitch which is mounted to the foot of a patient so that a tensioning mechanism may be attached to the ankle hitch for applying traction to the patient's leg.

Fractures and dislocations of leg bones and joints are desirably treated by applying a continuous longitudinal tension forced to the leg. Such traction eases the patient's pain, improves circulation in the injured leg and minimizes further injury to tissues which surround the injury, such as nerves and blood vessles, by the fractured ends of bones.

Traction may first be applied by emergency paramedics soon after they arrive at the scene of an injury. For this purpose, an ambulance is equipped with a traction splint which serves not only to immobilize the leg but additionally, extends beyond the bottom or sole of the patient's foot so that a resilient means, such as a spring, may be mounted in tension between the lowermost end of the splint and an ankle hitch secured about the patient's foot.

Traction is also a hospital treatment and is conveniently accomplished by means of a cable passing over a pulley which is rotatably mounted to the bed frame. A weight is attached at one end of the cable and the ankle hitch is attached at the other.

One ankle hitch currently being marketed comprises a pair of straps stitched together in a tee shape. It is operatively attached to the foot with the perpendicular strap extending downwardly over the posterior heel prominence into attachment with the tensioning device. Another currently marketed ankle hitch is a bootlike device mounted to a plate. Still other prior art devices are illustrated in the following U.S. Pat. Nos.: 2,723,663; 2,811,965; 3,612,046; 3,680,551; 3,720,206 and 3,762,403.

Each of these prior art devices is limited by one or more of several disadvantages. Many of the prior art devices fail to apply the traction force as a vector lying along the longitudinal axis of the associated leg of the patient without also applying a bending moment to the patient's foot. Such a bending moment rotates the patient's foot away from its comfortable natural position substantially perpendicular to the leg. For example, the strap of the tee shaped device described above which passes over a heel prominence applies an extreme pressure to the heel prominence, rotating the instep of the foot upwardly and causing hypertension of the Achilles' tendon. A similar twisting or rotation affect is caused by the device illustrated in U.S. Pat. Nos. 3,680,551 and 3,720,206.

Other ankle hitches which are capable of applying the tension force vector along the longitudinal axis of the leg, such as that shown in U.S. Pat. Nos. 3,612,046 fail to inhibit the rotation of the foot. What is needed is an ankle hitch which confines and retains the foot in a natural, comfortable position and simultaneously causes the traction force vector to be applied along the longitudinal axis of the leg.

Another deficiency of several of the prior art devices is that they permit the application of excessive compressive forces to the skin which restrict the blood circulation in the surface capillaries and eventually produce surface sores. For example, the strap of the tee shaped device described above will apply such pressure to the heel prominence causing a bed sore wound to this portion of the body.

The tee shaped device, like some other devices, also involves the risk that the strap will slip sideways from the heel prominence and allow dislocation and misalignment of the ankle hitch and frustration of the traction function.

Still other ankle hitches are limited in their practical value because their structure inherently requires that a variety of sizes be available for accommodating different sizes of feet and for accommodating a shoe being worn by the patient.

Finally, as with many medical accessories especially those devices used in emergency situations, it is desirable that the ankle hitch be easily and quickly installed with a minimum of patient movement being necessary.

SUMMARY AND OBJECTS OF THE INVENTION

Accordingly, it is an object of the present invention to provide an ankle hitch which is self-aligning, in that it applies the traction force as a resultant force vector aligned through the ankle bone and along the longitudinal axis of the leg.

Another object of the invention is to provide an ankle hitch which applies zero net movement to the foot so that it does not tend to twist, tilt, bend or rotate and which has no possibility for slipping into misalignment.

Still another object of the invention is to provide an ankle hitch which distributes the pressure applied to the patient's foot over the widest possible area and does so in a way that the ankle hitch conforms closely to the anatomical curvature of the foot and yet retains a high friction gripping relationship to the foot.

Still another object of the present invention is to provide an ankle hitch which may be quickly and easily attached to the foot of an injured person so that it may be most effectively applied as quickly as possible without requiring significant movement of the injured leg.

Still another object of the invention is to provide an ankle hitch which has the characteristic that a single size accommodates and fits any size of human foot, both with and without a shoe being worn on the foot.

The invention has a first relatively longer flexible strap having a fastener secured at each of its opposite ends and being sufficiently long to permit the first strap to be wrapped forwardly around the ankle of the foot, cross upon the instep of the foot with its ends extending downwardly beyond the bottom of the foot. The ankle hitch further has a pair of relatively shorter, flexible, heel straps substantially symmetrically secured at one end of each to a central segment of the first strap posteriorly of the axis of the associated human leg. Each of the heel straps has a fastener at its other end. The effective length of each of the straps permits all of the fasteners to be brought together beneath the foot with the straps under tension for connection to the traction mechanism whereby counterbalancing moments are applied to the foot with a resultant net traction force in substantial alignment with the axis of the associated human leg.

Further objects and features of the invention will be apparent from the following specification and claims when considered in connection with the accompanying drawings illustrating several embodiments of the invention.

Figure 1:
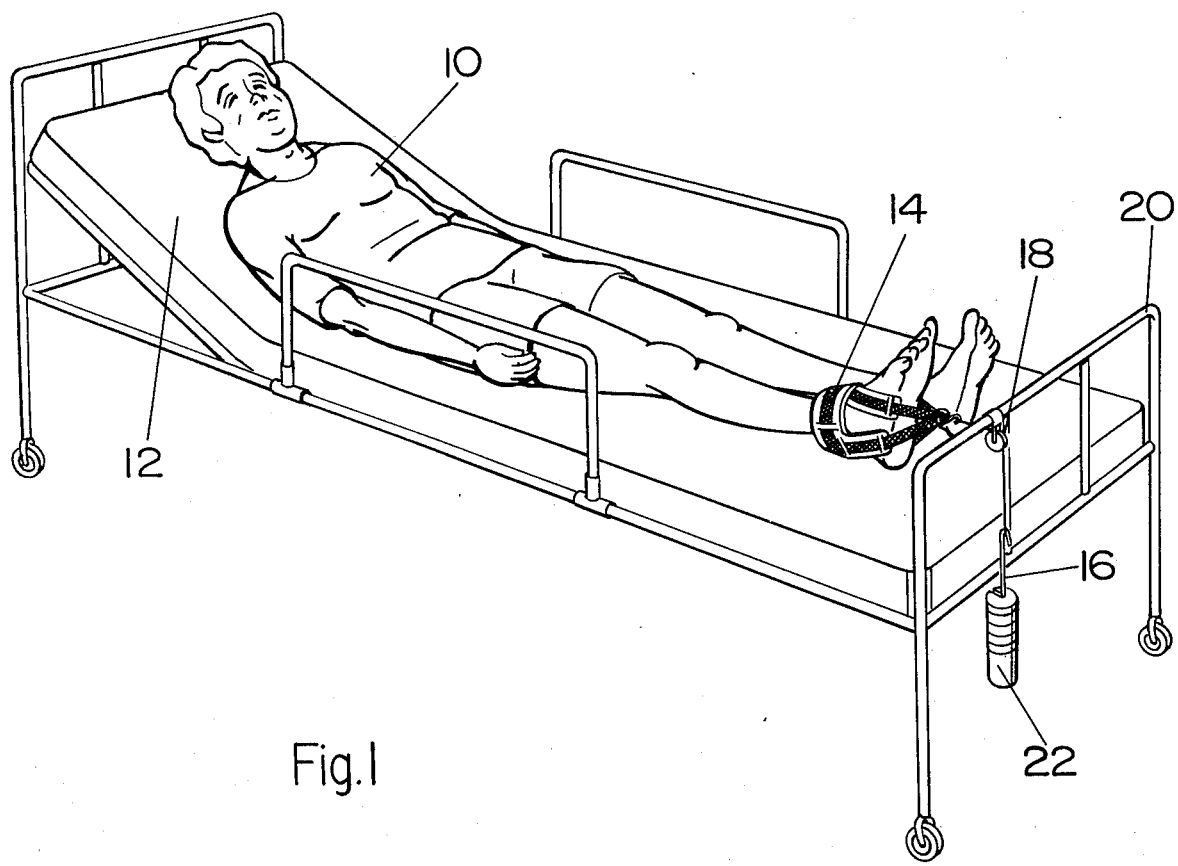
FIG. 1 is a view in perspective of a patient lying in a hospital bed having a traction weight and cable connected to an ankle hitch embodying the present invention which is mounted to the patient's foot.

In describing the embodiments of the invention illustrated in the drawings specific terminology will be resorted to for the sake of clarity. However, it is not intended to be limited to the specific terms so selected and it is to be understood that each specific term includes all technical equivalents which operate in a similar manner to accomplish a similar purpose.

DETAILED DESCRIPTION

FIG. 1 illustrates a patient 10 laying in a hospital bed 12 having an ankle hitch 14 embodying the present invention secured to his right foot. A flexible cable 16 extends over a pulley 18 rotatably mounted to the bed frame 20 and has a weight 22 fixed at one end and its other end in connection to the ankle hitch 14. The traction force is, of course, determined by the mass of the weight 22.

Figure 2:
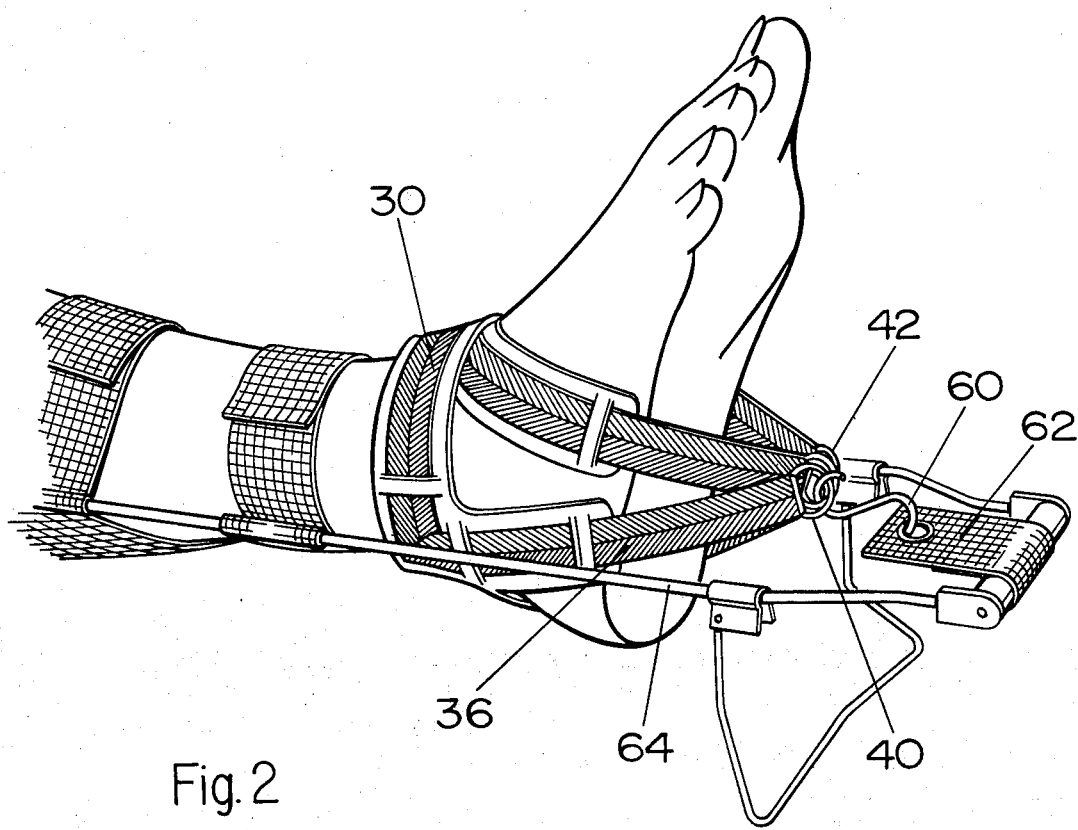
FIG. 2 is a view in perspective illustrating the connection of an ankle hitch embodying the present invention to a traction splint.
Figure 3:
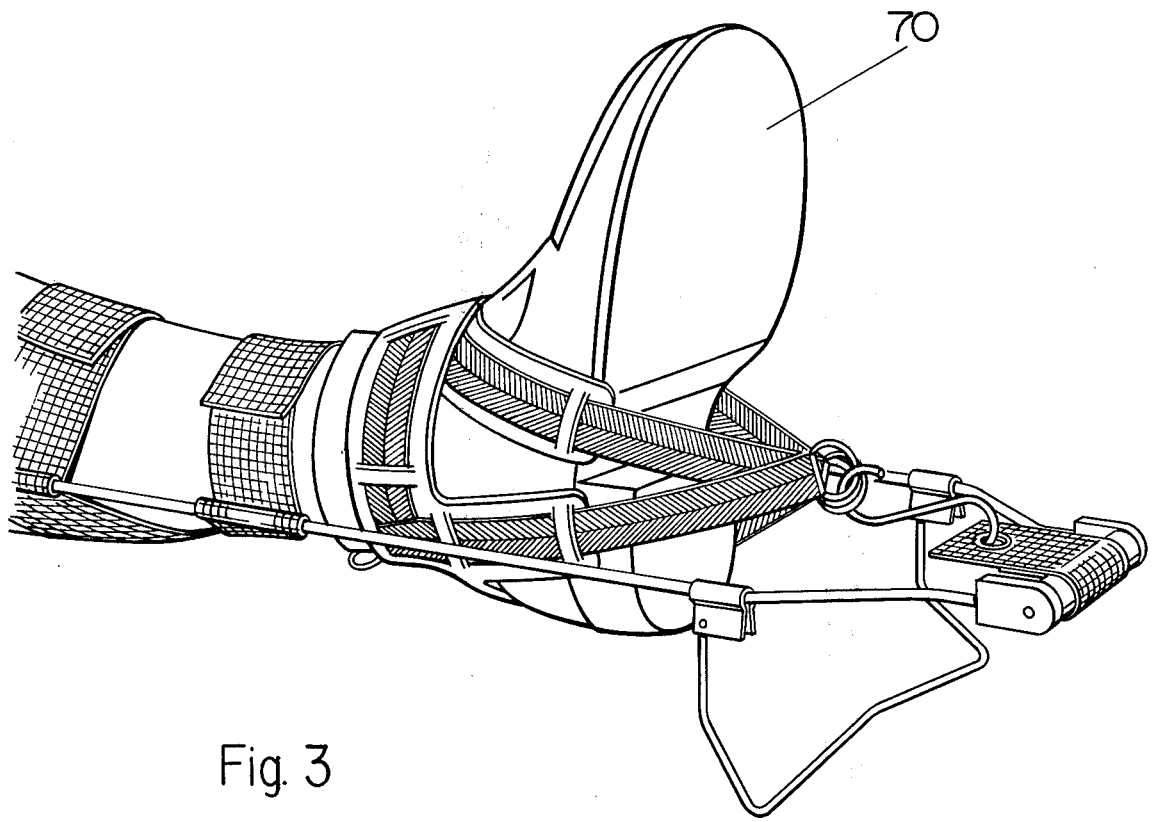
FIG. 3 is a view in perspective similar to FIG. 2 but illustrating the use of an ankle hitch embodying the present invention with a foot on which a shoe is worn.
Figure 4:
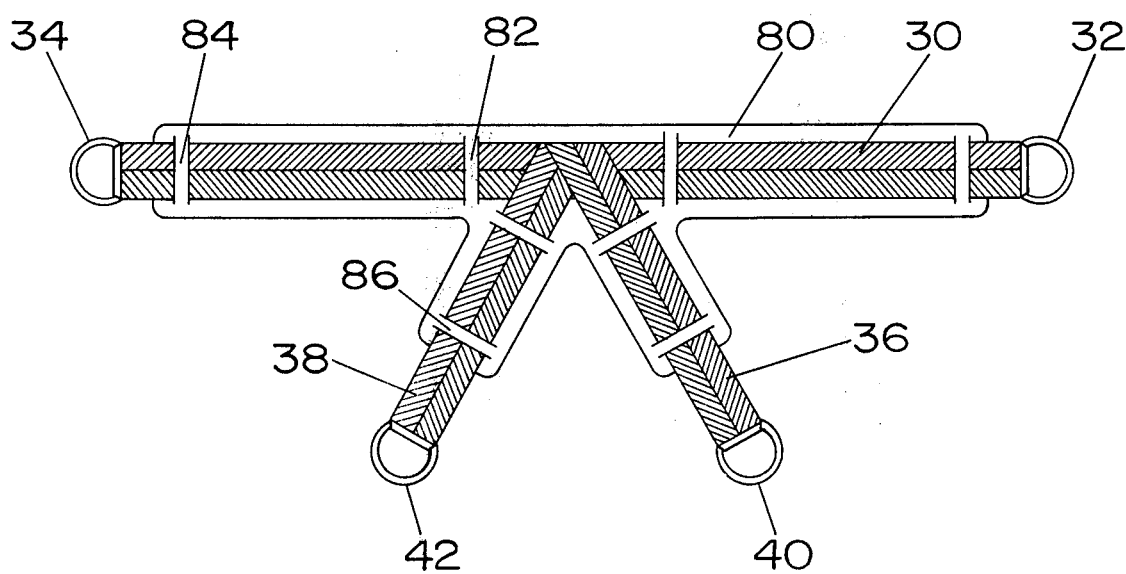
FIG. 4 is a plan view of the layout of the preferred embodiment of the invention.

Referring now to FIGS. 2–4, the preferred embodiment of the invention has a first, relatively longer, flexible strap 30 formed of a woven fabric webbing material. Fasteners 32 and 34, which are preferably D rings, are secured, such as by sewing, at each of the opposite ends of the first strap 30.

The first strap 30 is sufficiently long to permit, as illustrated in FIGS. 2 and 3, the first strap to be wrapped forwardly around the ankle of the foot, crossed upon the instep of the foot with its ends extending downwardly beyond the bottom of the foot.

The same woven fabric webbing may be used to form a pair of relatively shorter, flexible heel straps 36 and 38. Fasteners 40 and 42, such as D rings, are sewn or otherwise secured to one end of each of the heel straps 36 and 38.

In the preferred embodiment, the heel straps are secured substantially at the longitudinal center of the first strap 30 and are stitched to the first strap at opposite acute angles of 70°. This cooperation between the point to which the heel straps are attached and their angle of attachment permits the heel straps to apply a bending moment in one direction while the ends of the first strap apply a bending moment in the opposite direction. This force application causes cancellation of the bending moments while retaining the foot in its comfortable natural position. It permits all the fasteners to be aligned beneath the foot along an extension of the longitudinal axis of the leg so that the tension force vector may be applied along this longitudinal axis. The longitudinal axis of the leg passes substantially intermediate the ankle prominences which functionally define the hinge of the ankle.

It will become apparent however, that the heel straps may be otherwise positioned within a range of positions. The heel straps may be substantially symmetrically secured to a central segment of the first strap posteriorly of the longitudinal axis of the associated human leg and symmetrical about the substantial center of the first strap. Securing them more forwardly than the preferred rearmost position reduces the advantageous characteristics of the present invention somewhat in proportion to the distance such securing position is moved from the rearmost position. The term "symmetrically secured" means that wherever the heel straps are secured to the first strap, they are secured at positions which are substantially equally and oppositely spaced from the longitudinal center of the first strap.

Figure 5:
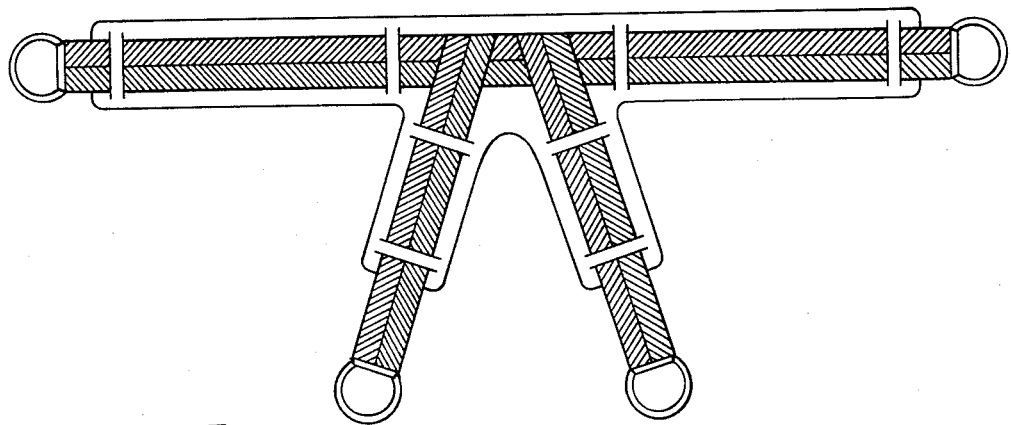
FIG. 5 is a plan view of an alternative embodiment of the invention.

Thus, for example, the ankle straps may be moved apart to the positions illustrated in FIG. 5.

Figure 6:
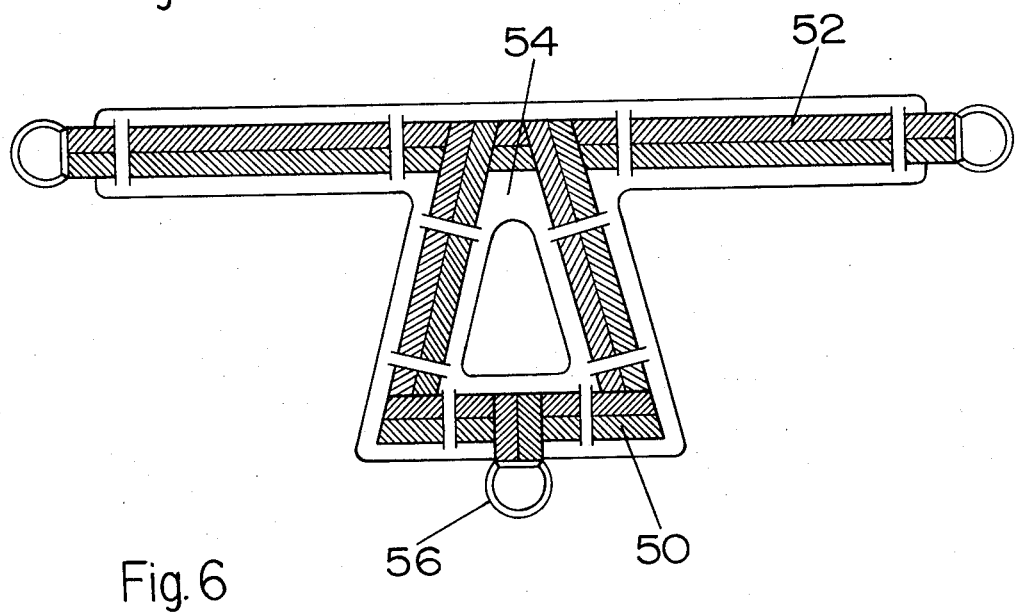
FIG. 6 is a plan view of another alternative embodiment of the invention.

As a further alternative illustrated in FIG. 6, a connecting segment 50 may be spaced from the first strap 52 and secured to both of the heel straps to provide a heel receiving opening 54. The connecting segment 52 could have a single fastener secured thereto.

Figure 7:
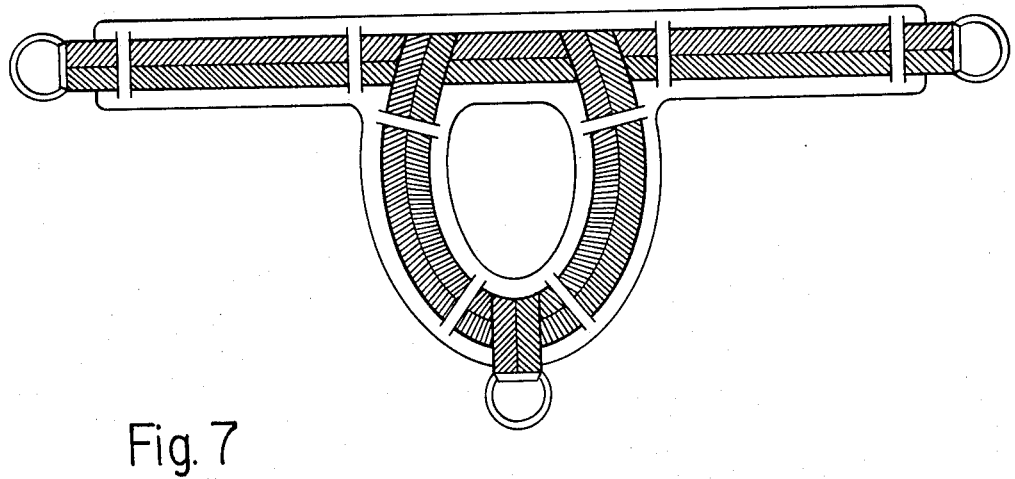
FIG. 7 is a plan view of yet another alternative embodiment of the invention.

In FIG. 7 there is illustrated yet another alternative embodiment of the invention wherein the ankle straps and connecting segment are blended or contoured into a single structure which is equivalent to the embodiment illustrated in FIG. 6.

Referring in particular to the preferred embodiment, the effective length of each of the straps is selected to permit all of the fasteners to be brought together beneath the foot with the straps under tension. For example, the first strap may be thirty inches long with each of the heel straps being effectively ten inches long after being sewn to the first strap. This causes counterbalancing moments to be applied to the foot with a resultant traction force in substantial alignment with the axis of the associated human leg for connection of the fasteners to the traction mechanism. Thus, for example, in FIG. 2, all the rings are brought together and connected to a metallic double hook 60 which in turn is connected to a resilient band 62 secured to the traction splint 64.

The device is identically arranged as illustrated in FIG. 3 when the patient is wearing a shoe 70 upon his foot. The only difference will be that each of the straps will extend a smaller distance below the bottom of the shoe sole than they do below the bottom of a bare foot but will still come together in alignment with the longitudinal axis of the leg.

In order to further distribute the forces applied to the surface of the foot, to provide a higher friction and softer more conforming surface and to maintain neatness and cleanliness, a flexible resilient foam layer 80 is attached to the straps for interposition between the straps 30, 36 and 38 and the foot when the ankle hitch is operatively attached to the foot. Preferably, the foam has a canvass backing bonded thereto and has a plurality of closely spaced lateral pairs of slits through the canvass and foam laminate to provide a plurality of spaced loops such as loops 82, 84 and 86 so that the foam layer is effectively removably attached to the straps. With this structure, the foam layer may be replaced when it becomes soiled or worn without necessitating replacement of the straps and fasteners secured thereto.

The ankle hitch comprising the preferred embodiment of the invention may be very quickly and easily mounted to the foot of a patient without the need of any snaps or fasteners or detachable connecting means for connecting the ankle hitch to the foot. The ankle hitch embodying the present invention simply encircles the ankle, overlaps at the instep with the straps extending downwardly to provide secure engagement with the foot. More specifically, the ankle hitch is first positioned with the stitched juncture of the heel straps with first strap posteriorly of the Achilles' tendon with the heel straps extending toward and past the bottom of the foot. The opposite ends of the first strap may be grasped and brought anteriorly, crossed above the instep and pulled downwardly beneath the arch of the foot. At this position, all four fastener rings are brought together and clipped to the tensioning device.

It is to be understood that while the detailed drawings and specific examples given describe preferred embodiments of the invention, they are for the purposes of illustration only, that the apparatus of the invention is not limited to the precise details and conditions disclosed and that various changes may be made therein without departing from the spirit of the invention which is defined by the following claims.

What is claimed is:

1. An ankle hitch for securing a human foot in attachment to a traction mechanism and comprising:
   a. a first relatively longer, flexible strap having a fastener secured at each of its opposite ends and being sufficiently long to permit said first strap to be wrapped forwardly around the ankle of said foot, crossed upon the instep of said foot with its ends extending downwardly beyond the bottom of said foot; and
   b. a pair of relatively shorter flexible heel straps substantially symmetrically secured at one end of each to a central segment of said first strap posteriorly of the axis of the associated human leg, each of said heel straps having a fastener at its other end; the effective length of each of said straps being of a length which permits all four of said fasteners to be brought together beneath said foot with the straps under tension for connection to said traction mechanism whereby counterbalancing moments are applied to said foot with a resultant traction force in substantial alignment with the axis of the associated human leg.

2. An ankle hitch for securing a human foot in attachment to a traction mechanism and comprising:
   a. a first relatively longer, flexible strap having a fastener secured at each of its opposite ends and being sufficiently long to permit said first strap to be wrapped forwardly around the ankle of said foot, crossed upon the instep of said foot with its ends extending downwardly beyond the bottom of said foot;
   b. a pair of relatively shorter flexible heel straps substantially symmetrically secured at one end of each to a central segment of said first strap posteriorly of the axis of the associated human leg; and
   c. a connecting segment, spaced from said first strap to provide a heel receiving opening secured to both of said heel straps and having a fastener secured thereto, the effective length of each said straps being of a length which permits all three of said fasteners to be brought together beneath said foot with the straps under tension for connection to said traction mechanism whereby counterbalancing moments are applied to said foot with a resultant traction force in substantial alignment with the axis of the associated human leg.

3. An ankle hitch according to claim 1 wherein said heel straps are secured substantially at the longitudinal center of said first strap at opposite acute angles and each has a separate fastener.

4. An ankle hitch according to claim 3 wherein said opposite acute angles are approximately 70°.

5. An ankle hitch according to claim 1 wherein said fasteners comprise rings attached to the ends of said straps.

6. An ankle hitch according to claim 1 wherein a flexible resilient foam layer is attached to said straps for interposition between said straps and said foot when said ankle hitch is operably attached to said foot.

7. An ankle hitch according to claim 6 wherein said foam layer is removably attached to said straps with detachable fastener means for detachment of said foam layer.

8. An ankle hitch according to claim 7 wherein each of said heel straps are secured substantially at the longitudinal center of said first strap at opposite acute angles of approximately 70°.

9. An ankle hitch according to claim 8 wherein said fasteners comprise rings, a different one of said rings attached to the end of each of said straps.

10. An ankle hitch according to claim 9 wherein said detachable fastener means comprises a plurality of spaced loops formed on said foam layer.

* * * * *